United States Patent [19]
Harding, Jr.

[11] Patent Number: 4,668,294
[45] Date of Patent: May 26, 1987

[54] RODENT REPELLENT PAINT AND BARS

[76] Inventor: Norman T. Harding, Jr., 2320 Laketon Rd., Pittsburgh, Pa. 15221

[21] Appl. No.: 913,363

[22] Filed: Sep. 30, 1986

Related U.S. Application Data

[63] Continuation-in-part of Ser. No. 745,356, Jun. 14, 1985, Pat. No. 4,654,080.

[51] Int. Cl.⁴ .................................................. C09D 5/14
[52] U.S. Cl. .................................... 106/15.05; 16/16; 16/237; 16/239; 424/195.1
[58] Field of Search .................... 106/15.05, 18.29, 16, 106/195, 237, 239; 424/195.1

[56] References Cited

U.S. PATENT DOCUMENTS

| | | | |
|---|---|---|---|
| 75,561 | 3/1868 | McKinsey | 424/195.1 |
| 136,185 | 2/1873 | Sears | 424/195.1 |
| 779,634 | 1/1905 | Allen | 424/161 |
| 1,506,575 | 8/1924 | Eberhardt | 424/195.1 |
| 1,871,949 | 8/1932 | Bottrell | 514/711 |
| 2,159,550 | 5/1939 | Cross | 424/195.1 |
| 4,378,374 | 3/1983 | Reggio et al. | 426/3 |

OTHER PUBLICATIONS

Rice, E. L., *Pest Control with Nature's Chemicals*, 7/85, pp. 16, 17, 186 and 187.

*Primary Examiner*—Lorenzo B. Hayes
*Attorney, Agent, or Firm*—Buell, Ziesenheim, Beck & Alstadt

[57] ABSTRACT

Rodent repellent paints and solid are disclosed which are comprised of thujone oil in pure form or in the form of cedar leaf oil in a suitable liquid or solid carrier such as lacquer, kerosene, alcohol, sodium silicate, paraffin or sawdust.

9 Claims, No Drawings

RODENT REPELLENT PAINT AND BARS

CROSS REFERENCE TO RELATED APPLICATION

This application is a continuation-in-part of my co-pending application Ser. No. 745,356, filed June 14, 1985, and allowed Aug. 7, 1986 now U.S. Pat. No. 4,654,080.

FIELD OF INVENTION

The present invention relates to a paint and a paraffin based solid having rodent repellent characteristics.

DESCRIPTION OF THE PRIOR ART

For many years numerous attempts have been made to keep rats and mice away from homes, storage bins and other areas. Most commonly, traps or poisons are used to kill the vermin. In addition to creating dead animal disposal problems, traps and poisons also pose dangers to children, pets and animals. Furthermore, traps and poisons must be monitored. Sprung traps must be reset and consumed poison must be replaced. Also, many people have found that for each rat they kill with traps or poison there are others in the area who survive.

Rather than try to kill the rodents which are present, a better approach is to deter them from entering the area. Certain plant extracts have been found to have repellent properties. Bottrell in U.S. Pat. No. 1,871,949 uses oil of peppermint to repell rodents. Cross in U.S. Pat. No. 2,159,550 teaches that extracts from the wood and fruit of the Areca catechu plant have repellent properties. Yet, neither of these materials have had any commercial success.

The art has also recognized that certain plants repel rodents. For example, pieces of the wormwood plant (Artemsia Absinthium) have been used as moth and rodent repellents. But, these pieces are only effective for a relatively short period of time, typically a few days.

The art has generally attributed the repellent charactersitics of the wormwood and other plants to the presence of alkyloids in the plant. Apparently, these alkyloids are poisonous. However, I have discovered that thujone oil, a natural oil of the wormwood plant and a component of cedar leaf oil from the cedar tree, not alkyloids, will repel rodents when used in the manner here described.

SUMMARY OF THE INVENTION

I provide a rodent repellent in either liquid or solid form by combining pure thujone oil or cedar leaf oil which contains thujone oil with a suitable liquid carrier such as sodium silicate, kerosene or lacquer or with a suitable carrier such as paraffin or sawdust.

I prefer to use a paint comprised of thujone oil and lacquer in a mixture having 25% to 40% thujone oil.

I prefer to combine thujone oil and sodium silicate in a ratio of 3 parts thujone oil for each 22 parts sodium silicate.

I also prefer to use from one to six parts thujone oil for each eight parts paraffin to form a repellent bar.

I also prefer to mix one ounce of thoujone oil per pound of sawdust which results in the oil being absorbed by the sawdust without becoming oily or sticky.

DESCRIPTION OF THE PREFERRED EMBODIMENTS

I have found that certain compositions of thujone oil or cedar leaf oil and either a liquid or solid carrier will repell rodents for a significant period of time. A combination of thujone oil or cedar leaf oil and lacquer when used like a paint will keep rodents away from the painted area for between three and five years. When these oils are combined with paraffin the product can be used like mothballs. Sawdust which has been infused with these oils can be packaged in packets made from cloth or other materials which are permeable to the scent of thujone oil. It can also be spread over the target area. The effective life of the solid products usually is six months to a year depending upon the environment.

To make these products, I first extract the oil from the plant source. Thujone oil is extracted from the wormwood plant and cedar leaf oil is obtained from the cedar tree. Thujone oil is also commercially available as it is used in perfume. Both oils have a similar aroma and can be used interchangeably. Then the oil is combined with a suitable carrier to form a repellent paint or solid.

A. The repellent paint.

I have found that lacquer is a suitable carrier for thujone oil and cedar leaf oil. The oil and lacquer are combined so that at least 25% of the mixture is oil. Then, the combination is applied to a surface like any standard paint. If the lacquer does not contain aromatic hydrocarbons, I have found that a ratio in excess of 31% oil clouds the lacquer and makes it unsuitable. Lacquers which contain aromatic hydrocarbons require more oil to be effective. For such lacquers one must use at least 40% oil.

I have found that lacquers which utilize alcohol as a solvent, alone or with other solvents, and either shellac, various gums, or cellulose as a film former work well. Three lacquer formulations I have used are given below:

EXAMPLE I film former 14 ounces cellulose per gallon of solvents
12 ounces Damar gum per gallon of solvents
6 ounces Ester gum per gallon of solvents
3 ounces Dibutylphthalate solvent 40% Petrol
20% Denatured alcohol
15% Ethyl acetate
20% Butyl acetate
5% n-Butyl propionate

EXAMPLE II 15.5 parts Shellac
6.0 parts Mastic Sandarac 1.0 parts Camphor
13.7 parts Benroin
72.5 parts Alcohol

EXAMPLE III 9.60% Cellulose Nitrate
7.30% Processed Linseed Oil
2.39% Maleic Ester Resin 1.20% Plasticizer
31.10% Aromatic Hydrocarbons
9.68% Alcohols
28.23% Esters
10.50% Ketones The formulation of Example III is sold under the name "1000 Gloss Lacquer".

Another suitable carrier is sodium silicate. I prefer to combine 12% oil and 88% sodium silicate to form a paint. However, any combination containing from 4% to 25% oil will be effective.

A third carrier is refined, clear, white kerosene. This material has traditionally been used as a carrier for insecticides and is sold under the trade name Insectosol. I prefer to use 2% thujone oil and 98% Insectosol or kerosene. However, any combination of from 1% to 20% thujone oil and the balance Insectosol or kerosene is effective.

Other petroleum based solvents in addition to alcohol and kerosene could also be used as a carrier. These solvents must be non-reactive with thujone oil and evaporate at room temperature or lower. They also must not leave an odorous residue which would overpower the odor of thujone oil. Ratios of 2% to 40% oil and the balance solvent will work. Because refined, clear white kerosene and denatured alcohol would have mild odors, they are most suitable carriers.

I have conducted several experiments to show the effectiveness of my rat and mice repellents. The first experiment consisted of three boxes with the entrances to each blocked with sheets of screen. The rats were placed in the middle box. The box on the left contained food and the walls of the box were stained with the rat and mice repellent. This repellent was a mixture of 12% thujone oil and 88% lacquer. The box on the right contained only food and the walls were not stained. At the end of five days, the metal screens were lifted. The rats would not enter the box with the rat and mice repellent, but ate from the box that contained no repellent.

In a second experiment, I used two boxes separated by a metal screen. A neutral box without repellent on the walls housed the rats. The remaining box contained the rate and mice repellent and contained the food. After five days the metal screen which separated the boxes was lifted. The rats would not enter the box stained with the rat and mice repellent to get the food. The repellent used in this experiment was a mixture of 12% thujone oil and 88% lacquer.

B. The repellent solids.

I have also found that a solid rodent repellent can be made by mixing thujone oil or cedar leaf oil with paraffin and molding the mixture to a desired shape, preferably a bar. I have found that a mixture of from 6% to 42% oil is effective. Compounds of from 1 to 6 parts oil of thujone for each 8 parts paraffin were particularly useful.

Experiments with a solid repellent having 6% thujone oil and 94% paraffin demonstrated the effectiveness of my repellant bars.

Another effective solid repellent can be made by soaking sawdust in pure thujone oil and allowing it to dry. Then the sawdust can be pressed into a bar or other desirable shape.

I prefer to use a mixture of one ounce of thujone oil for each pound of fine sawdust. When they are mixed, the sawdust absorbs the thujone oil but does not become sticky or oily. Although any ratio of thujone oil and sawdust will have rodent repellent properties, those combinations which do not result in a sticky or oily product are the easiest to handle. Various grades of sawdust can be used but the finer grades are preferable because they have more surface area per unit of weight. Wood chips could be substituted for sawdust but are less effective. Also, sawdust is readily available at little or no cost whereas wood chips are more expensive to obtain. These cost considerations make sawdust preferable to wood chips. The treated sawdust may be spread over the target area or it may be used in packets which allow the odor of thujone oil to escape. Cloth and filter paper are suitable materials for the package which then can be used without opening it. If other packaging materials are used it may be necessary to open or perforate the package before use.

While I have described certain present preferred embodiments of my invention it should be distinctly understood that the invention is not limited thereto but may be variously embodied within the scope of the following claims.

I claim:

1. A rodent repellent paint comprised of 25% to 31% thujone oil and 69% to 85% lacquer which contains no aromatic hydrocarbons and wherein the lacquer contains alcohol as a solvent and at least one film former selected from the group comprised of shellac, damar gum, ester gum, and cellulose nitrate.

2. The rodent repellent paint of claim 1 wherein at least a portion of the thujone oil is replaced with cedar leaf oil.

3. A rodent repellent paint comprised of from 2% to 40% thujone oil and 60% to 98% petroleum based solvent which solvent is non-reactive with thujone oil and which will evaporate at room temperature.

4. A rodent repellent paint comprised of at least 40% thujone oil and the balance lacquer which contains aromatic hydrocarbons and alcohol as solvent and at least one film former selected from the group comprised of shellac, damar gum, ester gum, and cellulose nitrate.

5. The rodent repellent paint of claim 3 wherein at least a portion of the thujone oil is replaced with cedar leaf oil.

6. A rodent repellent paint comprised of thujone oil, refined, clear white kerosene having a total concentration of from 1% to 20% thujone oil and from 80% to 99% kerosene.

7. The rodent repellent paint of claim 6 wherein at least a portion of the thujone oil is replaced with cedar leaf oil.

8. A rodent repellent solid comprised of sawdust impregnated with thujone oil.

9. The rodent repellent solid of claim 8 containing one ounce of thujone oil for each pound of sawdust.

* * * * *